United States Patent [19]

Maneval et al.

[11] Patent Number: 5,532,593
[45] Date of Patent: Jul. 2, 1996

[54] NUCLEAR MAGNETIC RESONANCE IMAGING RHEOMETER

[75] Inventors: James E. Maneval, Lewisburg, Pa.; Kathryn L. McCarthy; Michael J. McCarthy, both of Davis, Calif.; Robert L. Powell, Sacramento, Calif.

[73] Assignee: The Regents of The University of California, Oakland, Calif.

[21] Appl. No.: 146,497

[22] Filed: Nov. 1, 1993

[51] Int. Cl.$^6$ ................................................. G01V 3/00
[52] U.S. Cl. ........................................ 324/306; 324/300
[58] Field of Search .................................. 324/300, 306, 324/307, 309, 314, 315, 318

[56] References Cited

U.S. PATENT DOCUMENTS

| | | | |
|---|---|---|---|
| 4,516,582 | 5/1985 | Redington | 128/653 |
| 4,520,828 | 6/1985 | Burl et al. | 128/653 |
| 4,532,473 | 7/1985 | Wehrli et al. | 324/306 |
| 4,570,119 | 2/1986 | Wehrli et al. | 324/306 |
| 4,788,500 | 11/1988 | Patz et al. | 324/309 |
| 4,816,763 | 3/1989 | Longmore | 324/306 |
| 4,817,416 | 4/1989 | Blanch et al. | 73/55 |
| 5,170,122 | 12/1992 | Bernstein | 324/309 |
| 5,204,625 | 4/1993 | Cline et al. | 324/306 |
| 5,214,380 | 5/1993 | Dumoulin | 324/307 |
| 5,221,898 | 6/1993 | Takiguchi et al. | 324/306 |
| 5,277,058 | 1/1994 | Kalyon et al. | 73/54.11 |
| 5,375,598 | 12/1994 | Dumoulin et al. | 324/306 |

OTHER PUBLICATIONS

"NMR flow imaging of fluids and solid suspensions in poiseville flow" by Sinton et al. Rheology, vol. 35, No. 5, Jul. 1991 pp. 735–771.

"Rheological and Morphological Characterization of Selected Poly(organo) phosphazenes" Mujudmar et al. Polymer Eng. Sci. vol. 31 No. 10 May 1991.

"Calculation of Pressure Gradients from MR Velocity Data in a Laminar Flow Model" Adler et al. Jour. Comp. Ass. Tom. vol. 15 No. 3 1991.

"2Ds pulsatile hemodynamic analysis in the MR angiography interp. of a stenosed carotid arterial bifurcation" Tasciyan et al. Med. Phys. 20(4) Jul./Aug. 1993.

"NMR Velocity Spectra of Pulsatile Flow in a Rigid Tube" Wendt et al. 8306 Mag. Reson. Med. 27 Oct. 1992 No. 2.

Brunn et al., "Optical and Acoustic Rheometers: Three Examples" Rheology 93—Controlling Flow Properties, Mar. 1993.

*Primary Examiner*—Louis M. Arana
*Attorney, Agent, or Firm*—John P. O'Banion

[57] ABSTRACT

An apparatus and method for obtaining rheological information about a fluid using nuclear magnetic resonance is disclosed herein. A fluid flowing through a tube is subjected to nuclear magnetic resonance imaging signals to obtain the velocity profile of the fluid. The pressure gradient between two points along the tube is also obtained. The shear rate is then determined from the velocity profile, and the shear stress is determined from the pressure gradient. From a single velocity profile, data is obtained over shear rates ranging from zero at the center of the tube to the maximum shear rate at the tube wall. Alternatively, the velocity spectrum can be obtained and used in the same manner. The shear stress versus shear rate curve can thereby be obtained from a single nuclear magnetic resonance image taken at a specific value of the pressure gradient.

18 Claims, 5 Drawing Sheets

NUCLEAR MAGNETIC RESONANCE IMAGING RHEOMETER

This invention was made with Government support under Grant No. CTS-9057660, awarded by the National Science Foundation. The Government has certain rights in this invention.

BACKGROUND OF THE INVENTION

1. Field of the Invention

This invention pertains generally to measuring flow characteristics of viscous materials, and more particularly to non-invasive measurement of rheological information using nuclear magnetic resonance spectroscopy and imaging.

2. Description of the Background Art

Many important technologies involve the processing of non-Newtonian fluid materials which have difficult to characterize flow or rheological properties. Thermoplastics are a class of industrially important non-Newtonian fluids which exhibit a full range of theological properties including a steady shear viscosity, $\eta$, (or shear stress, $\sigma$) that depends upon shear rate, $\gamma$, dynamic viscoelastic properties, normal stresses and time dependent properties. Many slurries found in process industries, such as food and pulp slurries, also exhibit such complex rheology. Other effects, such as phase separation, may also be present due to the multiphase nature of the suspension.

The macroscopic rheology directly reflects the microstructure of the materials being processed. For a thermoplastic, the molecular weight, degree of polymer branching and molecular configuration all play important roles. Properties of suspensions are principally dominated by the particle concentration, size and morphology. Hence, the macrorheological properties are a significant indicator of a wide variety of factors to be monitored and controlled during processing. Further, these properties, particularly the shear viscosity, directly affects the performance of extruders, pumps and other processing equipment. Achieving a particular production rate and product quality requires knowing the viscosity so that the proper motor speeds, heating rates and other process variables can be specified. Therefore, the ability to monitor the viscosity is essential for control of unit operations and assuring product quality.

Process monitoring rheometers are generally categorized either as on-line or in-line devices. On-line rheometers monitor the properties of a side stream of material, whereas in-line rheometers monitor the properties at a point in the process itself. The actual rheological property that is measured varies; however, most instruments measure the steady shear viscosity. The principle is generally the same—a pressure drop is measured during flow through a slit or die. Also, in most, the viscosity is determined at a single shear rate (i.e., a "single point" measurement). The exceptions to this are the Rheometrics Melt Flow Monitor, the Güttfert Real Time Rheometer and the Brabender Auto-grader. The last is actually an in-line rheometer for monitoring the properties of feedstock (thermoplastic pellets or powders). The other two instruments are true in-line instruments in that they can be inserted in the process lines. Sidestreams are pumped through capillaries and returned to the main process stream. While these devices are capable of operating at more than one shear rate, however, pump speeds must be changed for each new shear rate. Other instruments determine either the elongational viscosity or the dynamic viscosity.

For most applications, the steady shear viscosity is the most useful measurement with precision process control and product monitoring potentially benefiting from the in-line measurement of viscosity over a wide range of shear rates. However, an adequate characterization of a thermoplastic can easily involve obtaining data over at least three decades of shear rates with several (at least five) points per decade.

In contrast, a typical on-line measurement of pressure drop and flow rate produces a single viscosity value at a single shear rate. With current technology, increasing the number of data points requires changing the flow rate by implementing auxiliary pumping capacity and acquiring data over a longer time or by cascading a series of capillaries, which still limits the number of data points to the number of capillaries.

Existing rheometers that are based upon fundamental principles and which perform measurements independent of a particular constitutive mode require many measurements in order to obtain similar information. For example, tube rheometers require that a series of flow rate measurements be made at different pressure gradients. This is very time consuming and completely impractical as an on-line process monitoring tool to measure the entire viscosity-shear rate curve. Similar limitations apply to rotational rheometers which require that torque be measured for various rotational speeds. Even the most up-to-date systems meet only the minimal requirements currently being advanced by researchers to characterize, for example, the molecular weight distribution of a thermoplastic.

The present invention overcomes the foregoing deficiencies in rheometers and rheological processing methods heretofore developed. Data can be obtained over a wide range of shear rates from a single measurement (flow rate or pressure drop). Further the invention can be applied to opaque as well as transparent systems, and hence can be used in applications ranging from thermoplastics to high density suspensions.

SUMMARY OF THE INVENTION

The present invention generally comprises an apparatus and method for obtaining macroscopic rheological information (primarily the shear stress-shear rate curve) about a fluid using nuclear magnetic resonance (NMR) spectroscopy and imaging measurements of the velocity spectrum and pressure gradient during tube flow. The velocity spectrum is a record of the velocities present during flow. For a tube of circular cross-section, measuring the velocity spectrum is equivalent to measuring the velocity profile. The velocity profile provides the shear rate distribution in the fluid while the pressure drop measurements determine the shear stress profile in the fluid. These two measurements are then used to directly provide the flow curve of the material.

The invention measures the macroscopic flow properties of a fluid in a non-invasive manner without reference to a particular model of fluid behavior, and can be used for experimental and analytical purposes as well as for process monitoring and control. Further, the invention provides a means for obtaining the viscosity-shear rate relation over a range of shear rates (zero at the tube center to the maximum shear rate a the tube wall) with a single measurement. Also, by varying the pressure gradient, the range of shear rates can be extended.

The apparatus of the present invention generally comprises a tube having (i) a uniform cross section along its length and (ii) a sufficient flow-development (entrance)

length from any reservoir used to hold the fluid to be measured, means for generating a flow through the tube such as a constant pressure pump that produces minimal vibration and oscillatory motion in the fluid, an RF probe encircling the tube, pressure sensors positioned on each side of the RF probe along the flow axis so that the pressure drop between the two points can be determined, a plurality of magnets for generating a magnetic field around the tube, magnetic field gradient coils positioned between the magnets and the RF probe, a power supply for the gradient coils, a transmitter and receiver coupled to the RF probe, and a central processing unit coupled to the transmitter and receiver and gradient coil power supply.

An important aspect of the method of the present invention is the NMR pulse sequence used to generate the velocity spectrum. This sequence is tailored so as to provide optimal data at each particular flow rate, and is repeated N times (where N is usually a power of 2), each time using a different strength, g, of the velocity-encoding gradient. For each repetition, the height of the signal at the echo time (TE) is recorded and the final set of echo heights is Fourier-transformed to yield the velocity spectrum.

As indicated above, for a rectilinear flow of a fluid in a tube of circular cross section, knowing the velocity spectrum is equivalent to knowing the velocity profile. Using the NMR pulse sequence, phase encode imaging is used to obtain the steady velocity profile in the tube. Given the velocity profile, w(r), the shear rate $\dot{\gamma}(r)$ is determined from the relationship $$\dot{\gamma}(r) = \frac{dw(r)}{dr} \quad (1)$$

where w is the axial velocity and r is the radial position in the tube. The shear stress, $\sigma$, as a function of the radial position in the tube, r, is $$\sigma(r) = -\frac{\Delta p}{2L} r \quad (2)$$

where P is the pressure at a point of measurement, L is the distance between the points of measurement, and $\Delta P/L$ is the pressure gradient.

Comparing equations (1) and (2), it can be seen that by eliminating r, the shear stress versus shear rate can be obtained. If we invert equation (2) and then substitute into equation (1), we find $\sigma(\gamma)$, or $\eta(\gamma) = \sigma(\gamma)/\gamma$. Hence, from a single image (velocity profile) taken at a specific value of $\Delta P/L$, data are obtained over shear rates ranging from zero to the maximum shear rate at the tube wall, r=R.

An object of the invention is to make non-invasive rheological measurements.

Another object of the invention is to obtain the shear stress—shear rate curve independent of a rheological model for the fluid.

Another object of the invention is to obtain the shear stress—shear rate relation for all values of shear rate from zero at the tube center to the maximum shear rate at the tube wall with one measurement.

Another object of the invention is to provide a simultaneous measurement of the shear stress—shear rate curve over the range of shear rates available in a tube.

Another object of the invention is to avoid the need to change measurement conditions over time to obtain a flow curve.

Another object of the invention is to obtain data over a wide range of shear rates from a single point (flow rate or pressure drop measurement).

Another object of the invention is to measure the shear stress—shear rate curve in opaque as well as transparent systems.

Another object of the invention is to make measurements in fluids ranging from thermoplastics to highly dense suspensions.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
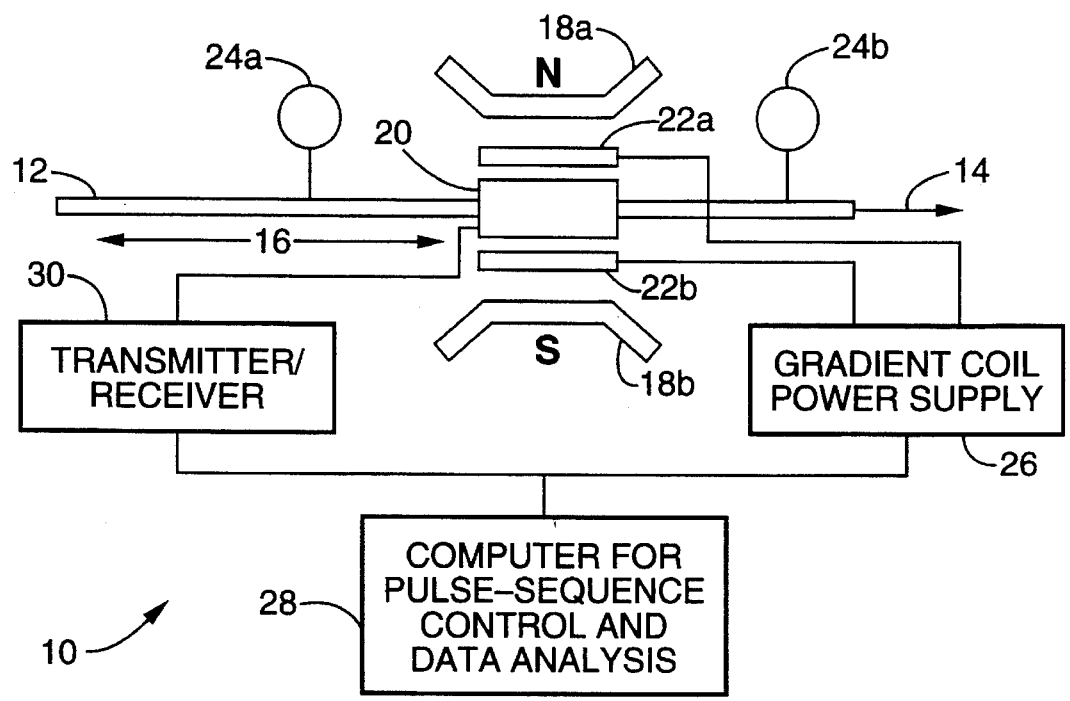
FIG. 1 is schematic diagram of a nuclear magnetic resonance flow rheometer in accordance with the present invention.

FIG. 1 schematically depicts a nuclear magnetic resonance flow rheometer 10 in accordance with the present invention. Magnetic resonance results from the interaction between atomic particles, electrons and the nuclei, and an external magnetic field. This interaction is similar to that observed when iron filings are placed near a bar magnet. The filings become oriented and a magnetic field is induced in the metal. However, unlike the physical motion of the filings, the physical orientation of the atomic particles is not altered. Only the magnetic moment of the atomic particles is influenced (at most common magnetic field strengths). Resonance is observed in these systems because they absorb and emit energy at specific frequencies. The specific frequency depends on the individual atomic particle and the strength of the applied magnetic field. When the atomic particle is a nucleus the phenomenon is termed Nuclear Magnetic Resonance (NMR). Not all nuclei exhibit magnetic resonance, however. A nuclei has a magnetic moment only if the spin angular moment is non-zero.

Nuclear magnetic resonance imaging (NMRI) is an NMR technique which provides spatial localization of the NMR signals from a sample. Signals from many neighboring spatial locations are used to generate an image of nuclei density or some other property. NMRI is based on degrading the homogeneity of the external magnetic field in a specific way, resulting in a known frequency variation across the sample. This variation is usually achieved by applying a linear magnetic field gradient. If the effects of the shielding constant are ignored, the frequency of excitation and detection for an NMR experiment, v, is given by the Larmor equation, $v = \gamma B_o/2\pi$, where $\gamma$ is the gyromagnetic ratio and $B_o$ is the magnetic field strength. By applying a linear field gradient in the z direction, the frequency becomes a function of position: $v(z) = \gamma(B_o + g_z z)2\pi$ where $g_z$ is the strength of the magnetic field gradient in the z direction. Using three orthogonal gradients during an NMR pulse sequence a two or three dimensional NMR image can be acquired. The principal advantage of NMRI is that the sample is unaffected by the measurement (at common magnetic field strengths) and opaque systems can be studied.

It is possible to use NMRI to measure directly velocity profiles in flowing systems using either a time-of-flight technique or phase encode imaging. In both of these techniques, the flowing fluid is subjected to a constant magnetic field of strength and a magnetic field gradient, g. After the spin systems have aligned with the imposed magnetic fields, they are disturbed by a radio frequency pulse that "tags" a region of the flow. Time-of-flight velocity imaging involves building a velocity image by successively exciting a particular cross-section of the flow and detecting the arrival of the excited spins downstream from where they were excited. By precisely knowing the $g_z$ downstream location of the detected signal and the time between excitation and detection, a velocity profile can be constructed for laminar, uni-directional flow.

Phase encode imaging produces direct images of velocity profile distributions for both uni-directional and more complex flows. In the case of one-dimensional, steady flows, this technique can be described as follows. Letting z(t) be the position of a spin at time t, then, $z(t) = Z_0 + w\,t$ where $Z_0$ is the position of the spin at time zero and w is the velocity of the spin. We call $g_z$ the applied magnetic field gradient in the flow direction, then, use Bloch equations to show that the phase of the magnetization is given by $$\phi = \gamma \int_0^t z(s) g_z(s) ds = \gamma(z_0 m_0 + w m_1) \qquad (3)$$

where $m_0$ and $m_1$ are the zeroth and first moments of the gradient, respectively, namely, $$m_0 = \int_0^t g_z(s) ds, \quad m_1 = \int_0^t s g_z(s) ds \qquad (4)$$

With phase encode imaging, the applied gradient is designed such that $m_0 = 0$ but $m_1 \neq 0$. Then, the phase angle is proportional to the velocity of the spin. Just as the phase of the magnetization can be used to measure the spin density distribution in standard NMRI, a properly designed gradient allows the phase to measure the distribution of velocities in a sample. We have applied this technique to a number of systems including Newtonian fluids, non-Newtonian suspensions, and single phase non-Newtonian fluids.

In a typical two-dimensional image of the joint spatial velocity density distribution of $^1$H from water in tube flow, the transverse (x) position is frequency encoded while axial velocity is phase encoded. The velocity profile is obtained by determining the maximum intensity for a given x position. The intensity at each position ideally reflects the number density of nuclei at a given position x with a velocity w. In reality the signal intensity represents a volume of fluid with a variation of velocities throughout the volume. If the velocity gradient is small, one essentially obtains a point value for the velocity profile. If the variation in velocities within the volume element is large an average velocity is reported.

As can be seen from FIG. 1, the NMR flow rheometer 10 includes a tube 12 through which a fluid 14 flows. Tube 12, which can be a capillary tube if desired, should preferably have a uniform cross-section along its length, and have a sufficient entrance length 16 from any reservoir to hold the fluid to be evaluated. Preferably, a gas cylinder or other constant-head device (not shown) is used to force the fluid 14 through the tube 12 so as to prevent fluid acceleration. If a constant pressure pump is used, the pump should produce minimal vibration or oscillatory motion in the fluid.

Permanent magnets 18a, 18b are radially positioned on each side of tube 12 to establish a magnetic field through the fluid 14, one magnet having its north pole facing the tube and the other magnet having is south pole facing the tube. Tube 12 extends through an RF probe 20, and gradient field coils 22a, 22b are positioned between magnets 18a, 18b and RF probe 22, respectively. In order to minimize the generation of unwanted eddy currents in magnets 18a, 18b, gradient field coils 22a, 22b (and hence RF probe 20) should be physically separated from magnets 18a, 18b by a distance sufficient to prevent coupling or the gradient field coils should be shielded. Preferably, the gradient strengths should be high (50 to 100 gauss/cm) so that low flow rates can be measured. Pressure sensors 24a, 24b, which are of a conventional type, are positioned at points along tube 12, one on each side of RF probe 20 for measuring the pressure gradient (drop) between those points. Also included is a power supply 26 for powering gradient field coils 22a, 22b. A control processor 28, which can be a central processing unit, microcomputer or the like, is used to generate the pulse sequences applied and to receive and evaluate fluid flow, pressure, and rheological data. Control processor 28 is coupled to a transmitter/receiver 30 and power supply 26. Power supply 26 is coupled to gradient field coils 22a, 22b and transmitter/receiver 30 is coupled to RF probe 20. Magnets 18a, 18b, RF probe 20, gradient field coils 22a, 22b, power supply 26, and transmitter/receiver 30 can be of a type used in conventional nuclear magnetic resonance imaging or spectroscopy equipment.

Figure 2:
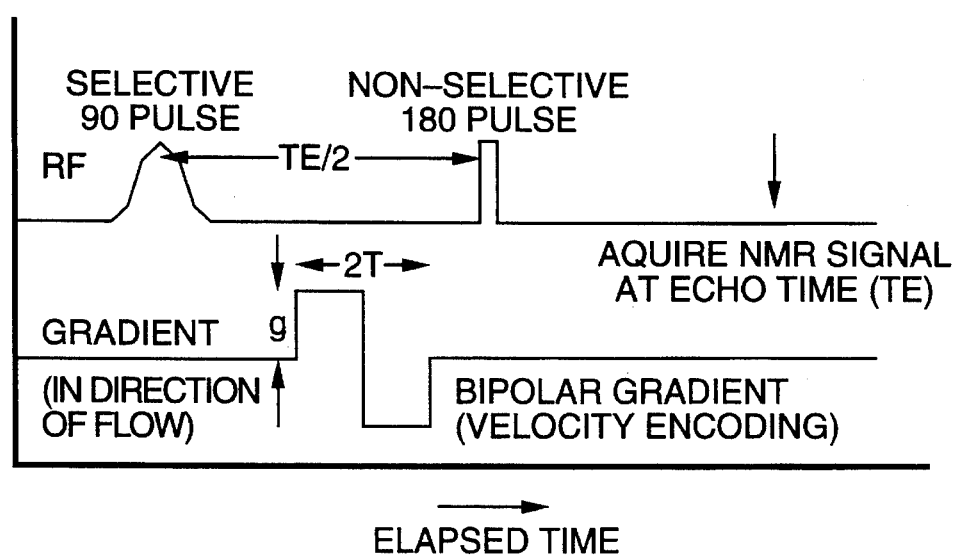
FIG. 2 is a timing diagram showing a pulse sequence used to measure a velocity profile using the apparatus shown in FIG. 1.

Referring to FIG. 2, an exemplary sequence of the RF and gradient pulses used to generate the velocity spectrum is shown. This sequence can be tailored so as to provide optimal data for any flow rate by setting the gradients used to measure only slightly more than the maximum velocity in the tube. The velocity sweep width would be set to be just greater than the maximum velocity. The frequency encode direction would have the minimum field of view necessary to prevent aliasing of the image. The sequence is repeated N times (where N is usually a power of 2), each time using a different strength, g, of the velocity-encoding gradient. For each repetition, the height of the signal at the echo time (TE) is recorded and the final set of echo heights is Fourier-transformed to yield the velocity spectrum. Gradient pulses should be short (10 ms) and sufficiently isolated from the RF pulses with respect to time. Also the bipolar gradient may be separated into two separate lobes, with one placed on each side of the 180° inversion pulse as shown. Slower flow rates can be measured by using longer echo times or by changing the pulse sequence to one based on the stimulated echo.

If desired, a spatial encoding gradient can be added in a direction orthogonal to the flow-encoding gradient. This is potentially useful for diagnosing instrument problems, as well as for stabilizing the echo through the use of a frequency encoding gradient during acquisition. Also note that the apparatus can be used for differential pressure measurement. In those cases where the constitutive relation is known for a fluid, the measurement made by the method described above can be interpreted in terms of a pressure drop across the measuring section.

EXAMPLE 1

We have tested this method using an aqueous polymer solution with phase encode imaging to measure the velocity profile. Tube flow was established using a flow loop consisting of 26.2 mm diameter Plexiglas tubing with the flow being driven by a sine pump. The tube is sufficiently long that the section in which the velocity profile is measured is over 175 diameters from the entrance region. An Oxford Instruments 2 Tesla magnet and a General Electric CSI-II Spectrometer were used to obtain phase encode $^1$H images. Two-dimensional images were generated by a standard spin-echo image sequence where the transverse (x) position was frequency encoded while the axial velocity was phase encoded. The non-encoded spatial position (y) causes the actual image intensity at any point (x,v) to be reflective of the range of velocities observable at a given x-value. However, for each s, there is a definable maximum velocity that allows us to obtain v(r) where $r=(x^2+y^2)^{1/2}$. Our measurements of velocity profiles were based on finding the highest velocity for a given x position and then taking this value as equivalent to v(r). The test fluid was a 3% by weight aqueous polyacrylamide solution (molecular weight $5.6 \times 10^6$). Its shear stress versus shear rate relation was characterized using a Weissenberg Rheogoniometer Model R 20 with a parallel plate geometry with appropriate formulas to account for the radial variation in the shear rate. Standard correction formulas were used in the calculation of the shear stress to account for the radial variation in the shear rate.

Figure 3:
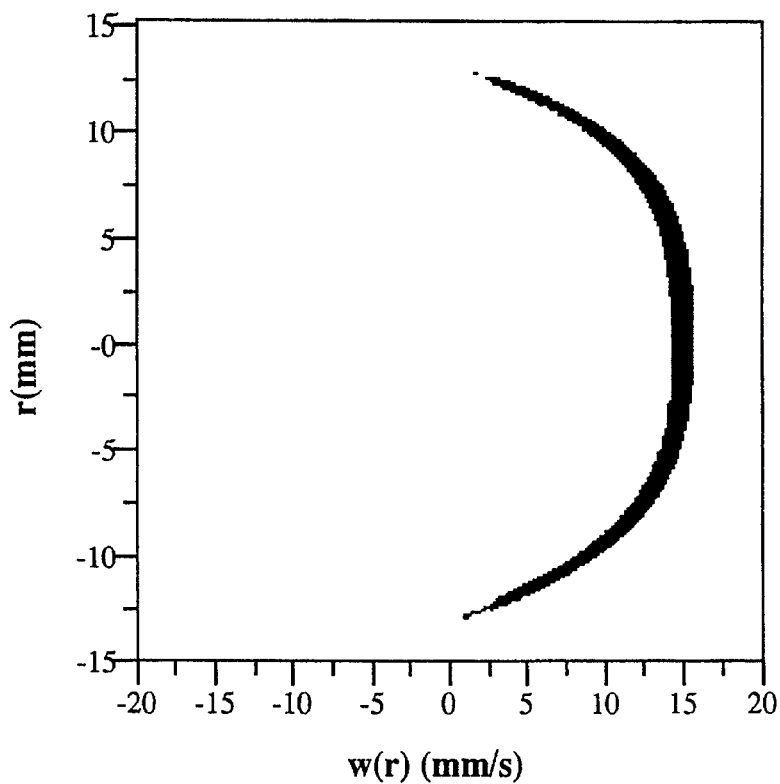
FIG. 3 is a graph showing a nuclear magnetic resonance imaging phase encode velocity profile for a steady, pressure driven flow of a 3% polyacrylamide solution in a tube using the method and apparatus of the present invention.

A sample velocity profile measured by the phase encode method is shown in FIG. 3 where the average velocity, <w>, is 100 mm/s. The radial position, r, is shown in millimeters, and the velocity profile, w(r), is shown in millimeters per second. As expected for a non-Newtonian shear thinning fluid, the velocity profile is blunted relative to the parabolic profile found for a Newtonian fluid. The sequence used 128 phase-encode steps and the final images were zero-filled to be 256×256. The vertical direction represents the distance across the tube with each pixel resolving 237 μm. Along the horizontal direction is the axial velocity, with the total resolution being ±200 mm/s and each pixel representing 0.315 mm/s. The profile is actually the projection of all of the velocities in a cross-section onto a plane. The broadening of the apparent profile is due to diffusion and experimental artifacts such as magnetic field inhomogeneity. The actual w(r) is ascertained by detecting the maximum intensity point in the center of the profile. There is no signal near the top and bottom of the image since this represents the region outside the tube.

The velocity gradient is determined by simple centered differences of the velocity profile. Higher-order difference schemes lead to little improvement over the centered difference method. All calculations were carried out using Matlab from Mathworks. The results for the shear rate versus the radial position can be seen in FIG. 4. The shear rates range from nearly $10^{-2}$ to over 10, or more than three decades. At the lowest shear rates near the center of the tube, the range is restricted by the resolution of the velocity and spatial measurements. The slope of the velocity profile in this region goes through zero, although numerically this value can only be approached.

Having determined γ(r) from equation (2), the next step is calculating σ(r) using equation (2). This requires either knowing ΔP/L or the flow rate. In our experiments, we measured the flow rate and determined the pressure drop using standard rheometrical formulas. While this was not the preferred implementation of the method of the present invention since some rheological information was required, our flow loop was not equipped with pressure measuring capabilities in the range required. However, we emphasize that the only assumption in our method is that viscometric theory rigorously holds for an aqueous polyacrylamide solution for which such anomalous effects as phase separation or wall slip would not be expected. The shear stress versus radial position for the flow conditions can also be seen in FIG. 4.

Figure 4:
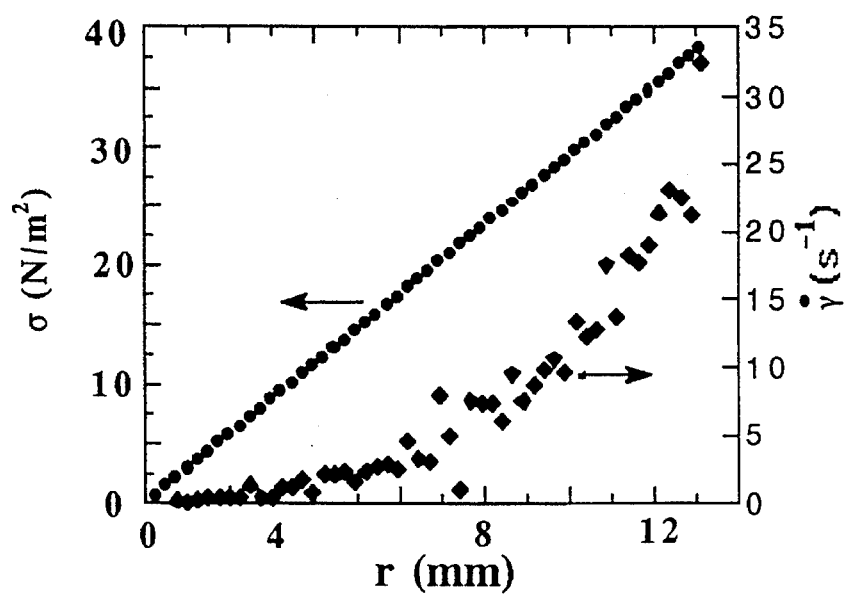
FIG. 4 is a graph showing shear stress and shear rate as functions of the radial position in a tube for a 3% polyacrylamide solution using the method and apparatus of the present invention.
Figure 5:
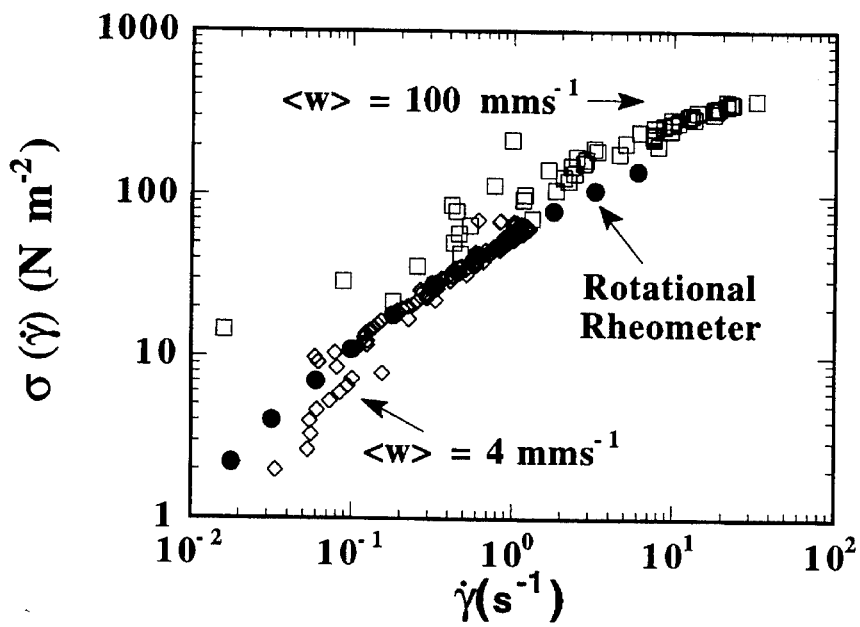
FIG. 5 is a graph showing shear stress versus shear rate for a 3% polyacrylamide solution obtained from the apparatus and method of the present invention and a conventional rotational rheometer.

The final step in analyzing the data comprises eliminating the radial variable in FIG. 4 to yield shear stress as a function of shear rate, σ(γ). This data is shown in FIG. 5 where open symbols represent data from the present invention and closed symbols represent data from a conventional rotational rheometer. Data is shown for two different average velocities, <w>=4 mm/s and <w>=100 mm/s. As can be seen, data from the present invention and the conventional rheometer data compare favorably. The principle discrepancy occurs at the lowest shear rates and for a range of intermediate shear rates. In both cases, data from the present invention corresponds to data at the lower shear rates—near the center of the tube—where equipment resolution can cause the largest errors. In the intermediate regimes, the data correspond exactly.

All of the data in FIG. 5 was obtained from two measurements with each resulting in many data points. The data span over three and one half decades of shear rate. Their number is determined by the number of voxels in the frequency encode direction and the field of view. The velocity resolution in the axial direction depends upon the number of phase encode steps and the velocity sweep width. Based on observations made regarding FIG. 4, it is likely that for a two point measurement, this range could easily be expanded to up to five decades by optimizing the mean velocities.

Therefore, it can be seen that a single point measurement will provide accurate data over three decades of shear rate.

Figure 6:
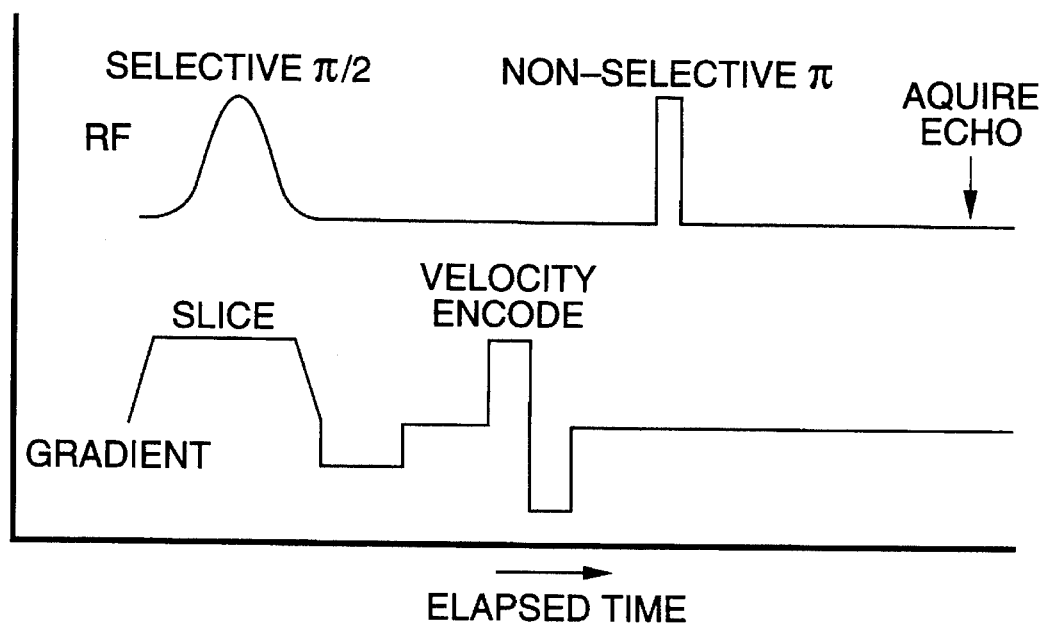
FIG. 6 is a timing diagram showing a pulse sequence to encode velocity for measurement of a velocity spectrum.

As an alternative to using the velocity profile, the velocity spectrum can be used. While the velocity profile is determined using nuclear magnetic resonance imaging, the velocity spectrum can be determined using either nuclear magnetic resonance imaging or spectroscopy. More so than the velocity profile method, this method relies upon some of the unique qualities of NMRI. Here, we use the pulse sequence shown in FIG. 6, which implements the phase encode velocity imaging with $m_0=0$ and $m_1 \neq 0$. For a single execution of this pulse sequence, the amplitude of the spin echo reflects the distribution of the velocities of the spins in the sample. Defining f(w) as the velocity spectrum, that is, f(w)dw is the fraction of spins in the sample between w and w+dw, and using the Bloch equations we find that the echo amplitude can be written as $$S(q_z) = \int f(w) \exp(i 2\pi q_z w) dw \qquad (5)$$

Here, $2\pi q_z = \gamma g_z T^2$ is a reciprocal velocity or the Fourier conjugate variable to the velocity and 2T is the duration of the velocity-encoding gradient. Repetition of the pulse sequence with different values of the gradient will "sweep out" the reciprocal domain and give the entire function $S(q_z)$. An inverse Fourier transform of this function then provides the velocity spectrum, f(w).

In order to utilize the velocity spectrum to obtain rheological information, we note that the signal amplitude can also be expressed as $$S(q_z) = \iint \rho(x,y) \exp(i\gamma g_z T^2 w) dx dy \qquad (6)$$

where, $\rho$ is the spin density. This relation generally holds for a velocity that depends upon both x and y. For tube flow, w=w(r) only, with $$r = \sqrt{x^2 + y^2} \qquad (7)$$

it is possible to establish a direct relation between the velocity spectrum and the velocity profile. For a homogeneous fluid, the spin density is constant in the tube and $dxdy = 2\pi r dr$. Therefore, equation (6) can be written as $$S(q_z) = 2\pi \int_0^R \rho \exp(i 2\pi q_z w(r)) r dr \qquad (8)$$

Changing the variable of integration from r to w, we can write $$S(q_z) = \frac{2}{R^2} \int_{w_{max}}^0 \exp(i 2\pi q_z w) r(w) \left| \frac{dw}{dr} \right|^{-1} dw \qquad (9)$$

where $w_{max}$ is the maximum velocity (i.e., the velocity at the tube center) and $$\left| \frac{dw}{dr} \right| \qquad (10)$$

is the Jacobian of the transformation from the r-coordinate to the w-coordinate. Comparing equations (5) and (9), it follows that $$f(w) = -\frac{2}{R} r(w) \left| \frac{dw}{dr} \right|^{-1} \qquad (11)$$

Since this development has been restricted to tube flow, it is straightforward to determine the precise form of the velocity spectrum using equation (11) once a constitutive relation has been chosen. Here, we consider three models that encompass a wide range of behavior, the Newtonian fluid, with $\sigma = \mu \gamma$, the power law model, $\sigma = m\gamma^n$ and plug flow, in which the velocity is constant across the tube. Table 1 provides the prediction of the velocity spectrum for each of these models. In this table, $\delta$ refers to the Dirac delta function.

Table 1 shows that the velocity spectrum depends strongly upon the constitutive model and hence upon the rheological properties of the fluid. From an NMRI standpoint, this provides the opportunity to use a measurement of the spectrum to directly characterize the properties of the fluid.

EXAMPLE 2

We have made these calculations for four cases, two shear thinning fluids with power law indices of ½ and ¾, a Newtonian fluid and a shear thickening fluid. Of particular interest are the results for the two shear thinning fluids. The velocity spectrum was found to be sensitive to the power law exponent, particularly near the center of the tube. For $w/w_{max} > 0.5$, this difference is more than a factor of two, which provides for considerable discrimination between these two types of fluids. A Newtonian fluid has a block spectrum, whereas a shear thickening fluid has a spectrum which decreases monotonically, as opposed to the shear thinning fluids for which f(w) increases monotonically.

Figure 7:
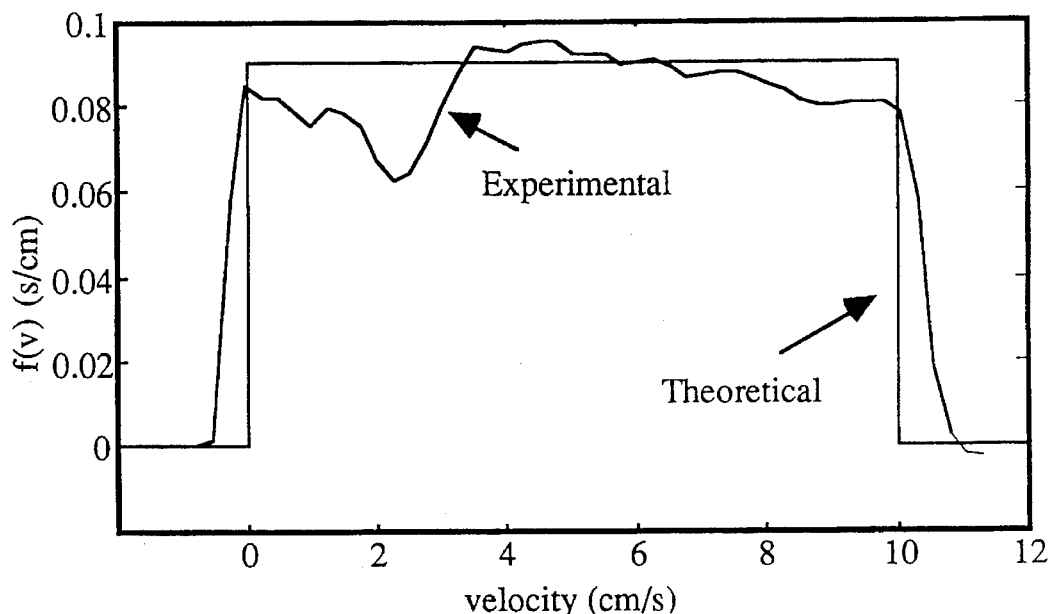
FIG. 7 is a graph comparing velocity spectra for laminar flow of water measured using the method and apparatus of the present invention with calculated values.
Figure 8:
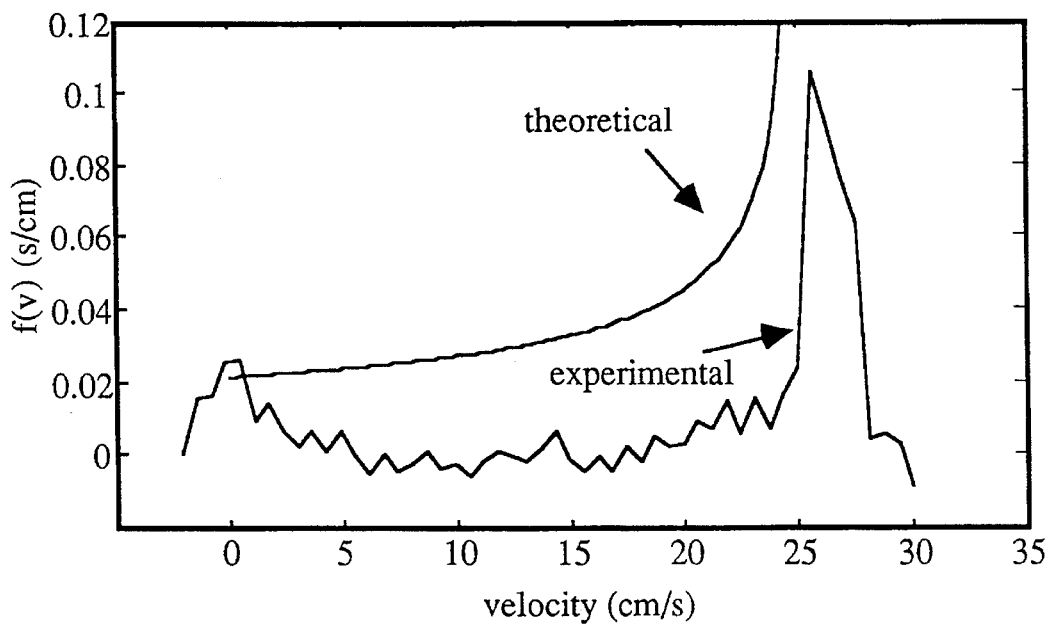
FIG. 8 is a graph comparing velocity spectra for tube flow of tomato juice measured using the method and apparatus of the present invention with calculated values.
Figure 9:
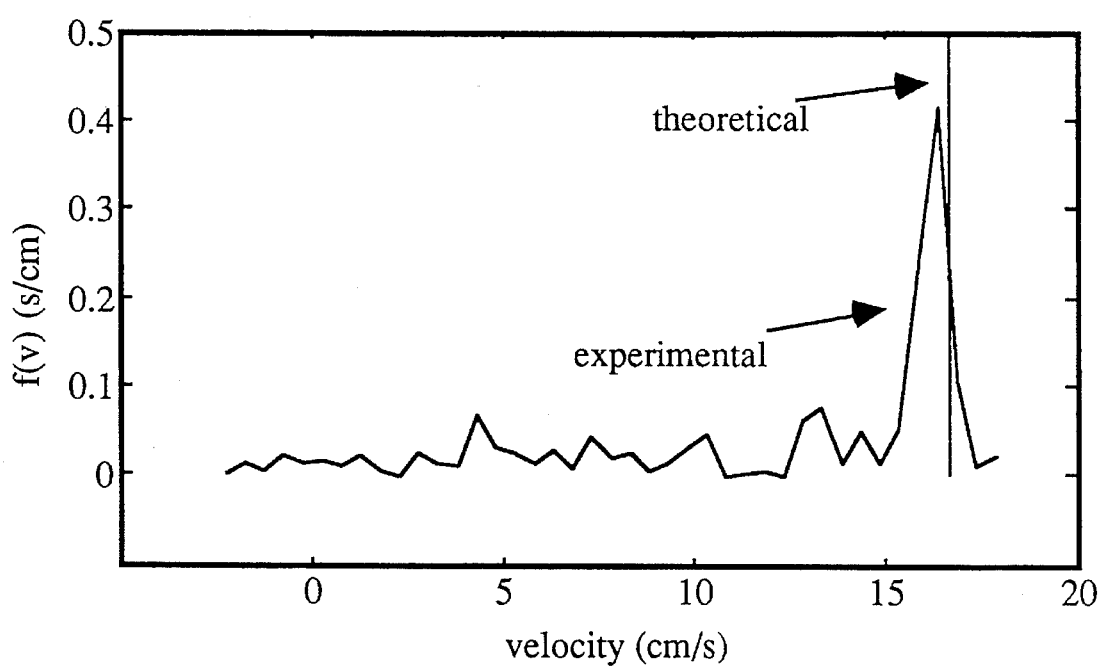
FIG. 9 is a graph comparing velocity spectra for tube flow of a pulp suspension measured using the method and apparatus of the present invention with calculated values.

FIG. 7 through FIG. 9 show velocity spectra for three types of materials: a Newtonian fluid (water), a shear thinning fluid (a 3% polyacrylamide solution) and a suspensions which flows as a plug (a 3% paper pulp suspension). In the first two cases, the spectra are seen to approximate those shown in FIG. 7 and FIG. 8. The spectrum for the Newtonian is a box-like spectrum and that for the power law fluid is monotonically increasing. Also shown on each figure are the predicted spectra, obtained using the theory presented above. In FIG. 9, the spectrum for the pulp suspension is peaked near $w/w_{max}$, however, as might be expected, it is difficult to resolve the actual "spike" predicted for such a flow, as presented in Table 1. For all of the cases shown in FIG. 7 through FIG. 9, the measured spectra follow the expected trends.

Accordingly, it will be seen that this invention provides for accurate determination of shear stress versus shear rate without the requiring multiple samples points. It will be appreciated that the method of the present invention may vary as to the steps and their sequence and that the apparatus of the present invention may vary as to configuration and as to details of the parts without departing from the basic concepts as disclosed herein. Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. An apparatus for measuring rheological characteristics of a fluid, comprising:

TABLE 1

| Constitutive Equation | w(r) | f(w) |
|---|---|---|
| Newtonian | $w_{max}\left(1 - \left(\frac{r}{R}\right)^2\right)$ | $\frac{1}{w_{max}}$ |
| Power-Law | $w_{max}\left(1 - \left(\frac{r}{R}\right)^{\frac{n+1}{n}}\right)$ | $2\frac{n}{n+1} \frac{1}{w_{max}} \left[1 - \frac{w}{w_{max}}\right]^{\frac{n-1}{n+1}}$ |
| Plug Flow | $w_{max}$ | $\delta(w - w_{max})$ |

(a) tube means for conducting the flow of a fluid, said fluid having an applied pressure gradient;

(b) imaging means for subjecting said fluid to nuclear magnetic resonance imaging and determining a velocity profile of said fluid as a function of radial position across said tube;

(c) pressure transducer means for measuring pressure of said fluid at a plurality of points along said tube and determining a pressure gradient between said points; and (d) processing means for converting said velocity profile to shear rate values for said fluid, for converting said pressure gradient to shear stress values for said fluid, and for determining a shear stress-shear rate curve for said fluid at said applied pressure gradient, wherein rheological properties of the fluid can be determined from said shear stress-shear rate curve.

2. An apparatus as recited in claim 1, wherein said shear rate values are determined according to $$\dot{\gamma}(r) \frac{dw(r)}{dr}$$

where w is the axial velocity of the fluid flowing through the tube, r is the radial position in the tube, and $\gamma(r)$ is the shear rate as a function of radial position in the tube.

3. An apparatus as recited in claim 1, wherein said shear stress values are determined according to $$\sigma(r) = -\frac{\Delta p}{2L} r$$

where P is the pressure at a point of measurement, L is the distance between the points of measurement, r is the radial position in the tube, $\Delta P/L$ is the pressure gradient, and $\sigma(r)$ is the shear stress as a function of radial position in the tube.

4. An apparatus for measuring rheological characteristics of a fluid using nuclear magnetic resonance imaging, comprising:

(a) tube means for conducting the flow of a fluid, said fluid having an applied pressure gradient;

(b) means for subjecting said fluid to nuclear magnetic resonance imaging and determining a velocity spectrum of said fluid;

(c) pressure transducer means for measuring pressure of said fluid at a plurality of points along said tube and determining a pressure gradient between said points; and (d) processing means for converting said velocity spectrum to shear rate values for said fluid, for converting said pressure gradient to shear stress values for said fluid, and for determining a shear stress-shear rate curve for said fluid at said applied pressure gradient, wherein rheological properties of the fluid can be determined from said shear stress-shear rate curve.

5. An apparatus as recited in claim 4, wherein said shear rate values are determined according to $$\dot{\gamma}(r) \frac{dw(r)}{dr}$$

where w is the axial velocity of the fluid flowing through the tube, r is the radial position in the tube, and $\gamma(r)$ is the shear rate as a function of radial position in the tube.

6. An apparatus as recited in claim 4, wherein said shear stress values are determined according to $$\sigma(r) = -\frac{\Delta p}{2L} r$$

where P is the pressure at a point of measurement, L is the distance between the points of measurement, r is the radial position in the tube, $\Delta P/L$ is the pressure gradient, and $\sigma(r)$ is the shear stress as a function of radial position in the tube.

7. An apparatus for measuring rheological characteristics of a fluid using nuclear magnetic resonance spectroscopy, comprising:

(a) tube means for conducting the flow of a fluid, said fluid having an applied pressure gradient;

(b) means for subjecting said fluid to nuclear magnetic resonance spectroscopy and determining a velocity spectrum of said fluid;

(c) pressure transducer means for measuring pressure of said fluid at a plurality of points along said tube and determining a pressure gradient between said points; and (d) processing means for converting said velocity spectrum to shear rate values for said fluid, for converting said pressure gradient to shear stress values for said fluid, and for determining a shear stress-shear rate curve for said fluid at said applied pressure gradient, wherein rheological properties of the fluid can be determined from said shear stress-shear rate curve.

8. An apparatus as recited in claim 7, wherein said shear rate values are determined according to $$\dot{\gamma}(r) \frac{dw(r)}{dr}$$

where w is the axial velocity of the fluid flowing through the tube, r is the radial position in the tube, and $\gamma(r)$ is the shear rate as a function of radial position in the tube.

9. An apparatus as recited in claim 7, wherein said shear stress values are determined according to $$\sigma(r) = -\frac{\Delta p}{2L} r$$

where P is the pressure at a point of measurement, L is the distance between the points of measurement, r is the radial position in the tube, $\Delta P/L$ is the pressure gradient, and $\sigma(r)$ is the shear stress as a function of radial position in the tube.

10. A method for determining rheological characteristics of a fluid flowing through a tube, comprising the steps of:

(a) subjecting a fluid flowing through a tube to nuclear magnetic resonance imaging and determining a velocity profile of said fluid as a function of radial position across said tube, said fluid having an applied pressure gradient;

(b) measuring pressure of said fluid at a plurality of points along said tube and determining a pressure gradient between said points;

(c) converting said velocity profile to shear rate values for said fluid;

(d) converting said pressure gradient to shear stress values for said fluid;

(e) determining a shear stress-shear rate curve for said fluid at said applied pressure gradient; and (f) determining rheological properties of the fluid from said shear stress-shear rate curve.

11. A method as recited in claim 10, wherein said shear rate values are determined according to $$\dot\gamma(r) \frac{dw(r)}{dr}$$

where w is the axial velocity of the fluid flowing through the tube, r is the radial position in the tube, and γ(r) is the shear rate as a function of radial position in the tube.

12. A method as recited in claim 10, wherein said shear stress values are determined according to $$\sigma(r) = -\frac{\Delta p}{2L} r$$

where P is the pressure at a point of measurement, L is the distance between the points of measurement, r is the radial position in the tube, ΔP/L is the pressure gradient, and σ(r) is the shear stress as a function of radial position in the tube.

13. A method for determining rheological characteristics of a fluid flowing through a tube using nuclear magnetic resonance imaging, comprising the steps of:
 (a) subjecting a fluid flowing through a tube to nuclear magnetic resonance imaging and determining a velocity spectrum of said fluid, said fluid having an applied pressure gradient;
 (b) measuring pressure of said fluid at a plurality of points along said tube and determining a pressure gradient between said points;
 (c) converting said velocity spectrum to shear rate values for said fluid;
 (d) converting said pressure gradient to shear stress values for said fluid;
 (e) determining a shear stress-shear rate curve for said fluid at said applied pressure gradient; and
 (f) determining rheological properties of the fluid from said shear stress-shear rate curve.

14. A method as recited in claim 13, wherein said shear rate values are determined according to $$\dot\gamma(r) \frac{dw(r)}{dr}$$

where w is the axial velocity of the fluid flowing through the tube, r is the radial position in the tube, and γ(r) is the shear rate as a function of radial position in the tube.

15. A method as recited in claim 14, wherein said shear stress values are determined according to $$\sigma(r) = -\frac{\Delta p}{2L} r$$

where P is the pressure at a point of measurement, L is the distance between the points of measurement, r is the radial position in the tube, ΔP/L is the pressure gradient, and σ(r) is the shear stress as a function of radial position in the tube.

16. A method for determining rheological characteristics of a fluid flowing through a tube using nuclear magnetic resonance spectroscopy, comprising the steps of:
 (a) subjecting a fluid flowing through a tube to nuclear magnetic resonance spectroscopy and determining a velocity spectrum of said fluid, said fluid having an applied pressure gradient;
 (b) measuring pressure of said fluid at a plurality of points along said tube and determining a pressure gradient between said points;
 (c) converting said velocity spectrum to shear rate values for said fluid;
 (d) converting said pressure gradient to shear stress values for said fluid;
 (e) determining a shear stress-shear rate curve for said fluid at said applied pressure gradient; and
 (f) determining rheological properties of the fluid from said shear stress-shear rate curve.

17. A method as recited in claim 16, wherein said shear rate values are determined according to $$\dot\gamma(r) \frac{dw(r)}{dr}$$

where w is the axial velocity of the fluid flowing through the tube, r is the radial position in the tube, and γ(r) is the shear rate as a function of radial position in the tube.

18. A method as recited in claim 17, wherein said shear stress values are determined according to $$\sigma(r) = -\frac{\Delta p}{2L} r$$

where P is the pressure at a point of measurement, L is the distance between the points of measurement, r is the radial position in the tube, ΔP/L is the pressure gradient, and σ(r) is the shear stress as a function of radial position in the tube.

* * * * *